(12) United States Patent
Tien et al.

(10) Patent No.: US 8,965,102 B2
(45) Date of Patent: Feb. 24, 2015

(54) SYSTEM AND METHOD FOR DEFECT ANALYSIS OF A SUBSTRATE

(71) Applicant: Taiwan Semiconductor Manufacturing Company, Ltd., Hsin-Chu (TW)

(72) Inventors: Yan-Wei Tien, Hualien (TW); Chi-Hung Liao, Sanchong (TW); Ming-Yi Lee, Xin Zhu Shi (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 122 days.

(21) Appl. No.: 13/673,664

(22) Filed: Nov. 9, 2012

(65) Prior Publication Data

US 2014/0133736 A1 May 15, 2014

(51) Int. Cl.
*G06K 9/00* (2006.01)
*G01N 21/00* (2006.01)
*G06K 9/03* (2006.01)

(52) U.S. Cl.
CPC ........................................ *G06K 9/03* (2013.01)
USPC ......... 382/149; 382/144; 382/168; 356/237.1

(58) Field of Classification Search
CPC ....... G06K 9/036; G06K 9/2036; G06K 9/03; G06T 7/001; G06T 2207/30148; G03F 1/84; G03F 7/705; G03F 1/36; G03F 7/70441; G03F 7/7065; G03F 7/70666
USPC ......... 382/144, 145, 141, 149, 168, 100, 103, 382/147, 148, 151, 199, 274, 209, 213, 232, 382/264; 716/51, 52, 53, 56, 54, 55, 139; 430/5, 30, 311, 322; 356/237.1, 237.4, 356/237.5; 703/6, 13; 348/E7.085, 126, 128
See application file for complete search history.

(56) References Cited

U.S. PATENT DOCUMENTS

| | | | |
|---|---|---|---|
| 6,268,093 B1 | 7/2001 | Kenan et al. | |
| 6,373,975 B1 | 4/2002 | Bula et al. | |
| 6,757,645 B2 | 6/2004 | Chang et al. | |
| 6,873,720 B2 | 3/2005 | Cai et al. | |
| 7,012,683 B2 * | 3/2006 | Wolf et al. | 356/237.2 |
| 7,646,906 B2 * | 1/2010 | Saidin et al. | 382/144 |
| 8,139,843 B2 * | 3/2012 | Kulkarni et al. | 382/144 |
| 8,213,704 B2 | 7/2012 | Peterson et al. | |
| 8,671,366 B2 * | 3/2014 | Tanaka et al. | 716/54 |
| 2008/0205743 A1 | 8/2008 | Huang et al. | |

* cited by examiner

*Primary Examiner* — Sheela Chawan
(74) *Attorney, Agent, or Firm* — Haynes and Boone, LLP

(57) ABSTRACT

The present disclosure provides a method including providing a first image and a second image. The first image is of a substrate having a defect and the second image is of a reference substrate. A difference between the first image and the second image is determined. A simulation model is used to generate a simulation curve corresponding to the difference and the substrate dispositioned based on the simulation curve. In another embodiment, the scan of a substrate is used to generate a statistical process control chart.

10 Claims, 15 Drawing Sheets

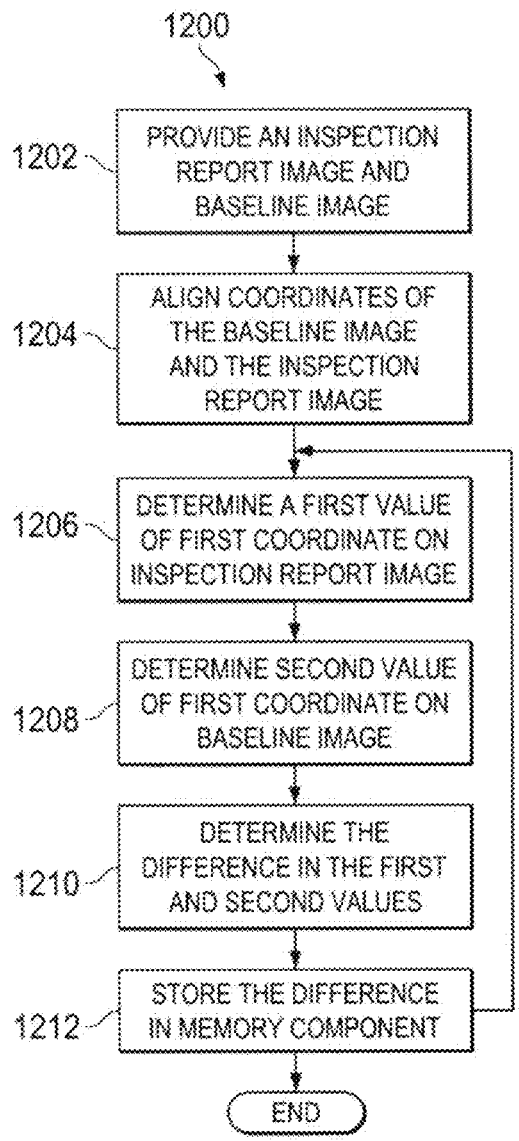
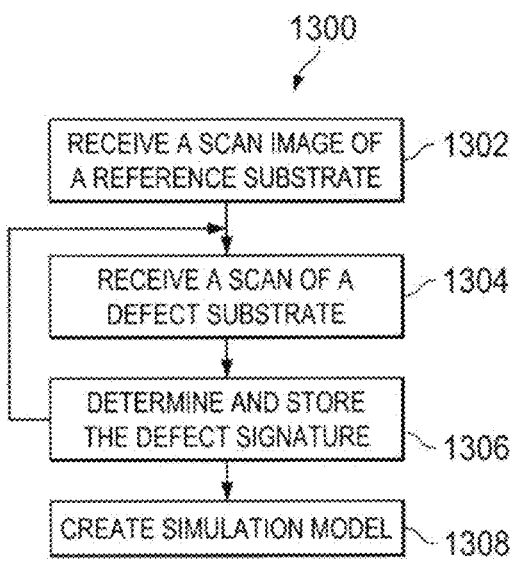
Fig. 12
Fig. 13

SYSTEM AND METHOD FOR DEFECT ANALYSIS OF A SUBSTRATE

BACKGROUND

This application relates to methods and systems for detecting and analyzing defects in substrates used in semiconductor device fabrication including reticle or photomask substrates and device substrates. The quality of the semiconductor device substrates and the photomasks used in the fabrication of the devices are verified at various points during the fabrication process. Traditional methods employed in the inspection of complex substrate patterns on wafers and/or masks are typically tremendously demanding in terms of time, complexity, and cost. The challenges of these inspections continue to increase as the patterns provided on the substrates decrease in size and increase in density. For example, as the technology nodes shrink, smaller and smaller defects in a photomask or device substrate can negatively affect the performance, yield, or reliability of the device.

Thus, what is a desired are systems and method for detecting and/or analyzing defects of substrates.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 12 is a flow chart illustrating an embodiment of a method of determining the difference in scan images according to one or more aspects of the present disclosure.

FIG. 13 is a flow chart illustrating an embodiment of a method of generating a simulation model according to one or more aspects of the present disclosure.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Various features may be arbitrarily drawn in different scales for simplicity and clarity.

Figure 1:
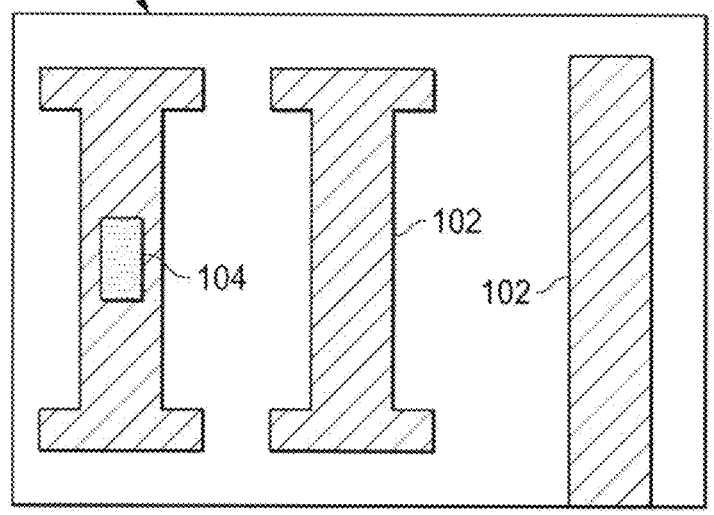
FIGS. 1 and 2 are exemplary embodiments of substrates having a defect suitable for analysis by one or more aspects of the present disclosure.
Figure 2:
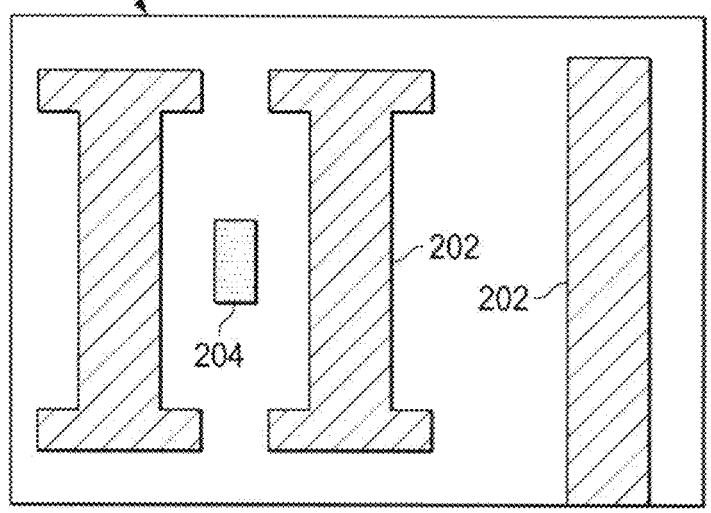

Illustrated in FIGS. 1 and 2 are exemplary embodiments of a substrate used in the fabrication of semiconductor devices. The substrates include defects that may be identified and/or analyzed using one or more of the methods and systems described herein. It is noted that these defects are exemplary only and not intended to be limiting.

Referring to FIG. 1 illustrated is a substrate 100 having a plurality of features 102 disposed thereon. A defect 104 is present in one of the features. The defect 104 may be referred to as a pin-hole defect (e.g., defective area has a void or blank area in which the feature should be formed).

In an embodiment, the substrate 100 is a photomask or reticle. The substrate 100 may be a transparent substrate such as fused silica ($SiO_2$), or quartz, relatively free of defects, calcium fluoride, and/or other suitable material used in a photolithography process. The features 102 may include attenuating material operable to pattern an incident radiation beam. The attenuating material may include chrome or other materials such as, for example, Au, MoSi, CrN, Mo, $Nb_2O_5$, Ti, Ta, $MoO_3$, MoN, $Cr_2O_3$, TiN, ZrN, $TiO_2$, TaN, $Ta_2O_5$, NbN, $Si_3N_4$, ZrN, $Al_2O_3N$, $Al_2O_3R$, or combinations thereof.

In another embodiment, the substrate 100 is a device substrate such as a semiconductor substrate (e.g., wafer). The substrate may be a semiconductor substrate that includes an elementary semiconductor including silicon and/or germanium in crystal; a compound semiconductor including silicon carbide, gallium arsenic, gallium phosphide, indium phosphide, indium arsenide, and/or indium antimonide; an alloy semiconductor including SiGe, GaAsP, AlIn As, AlGaAs, GaInAs, GaInP, and/or GaInAsP; or combinations thereof. The substrate may be strained, may be a semiconductor on insulator (SOI), have an epitaxial layer, and/or have other features enhancing performance. The substrate may include any number of semiconductor device features or portions thereof, for example, transistors including gate structures, doped regions such as source/drain regions, diodes including light emitting diode (LED) structures, memory cells, sensors, microelectromechanical systems (MEMS), and the like. The substrate may include any number of layers such as, conductive layers, insulating layers, etch stop layers, capping layers, diffusion/barrier layers, gate layers, hard mask layers, interfacial layers, and/or numerous other suitable layers. Alternatively, although processing a substrate in the form of a semiconductor wafer may be described; it is to be understood, that other examples of substrates and processes may benefit from the present invention such as, for example, printed circuit board substrates, damascene processes, and thin film transistor liquid crystal display (TFT-LCD) substrates and processes.

In an embodiment directed to a device substrate, the features 102 may include features, or portions thereof, of a semiconductor device(s) formed on the substrate 100. The semiconductor device(s) may include active or passive devices. For example, the semiconductor device may include passive components such as resistors, capacitors, inducers, fuses and/or active devices such as p-channel field effect transistors (PFETs), n-channel transistors (NFETs), metal-oxide-semiconductor field effect transistors (MOSFETs), complementary metal-oxide-semiconductor transistors (CMOSs), high voltage transistors, high frequency transistors, and/or other suitable components or portions thereof. In an embodiment, the features 102 are gate features associated with one or more transistors formed on the substrate. In another embodiment, the features 102 are interconnect features associated with one or more transistors formed on the substrate. The features 102 may include conductive material, semi-conductive material, or insulating material.

Referring to FIG. 2 illustrated is a substrate 200 having a plurality of features 202 disposed thereon. A defect 204 is present on the substrate 200. The defect 204 may be referred to as a pin-dot (e.g., material or debris formed in an unwanted region of the substrate).

The substrate 200 may be substantially similar to as discussed above with reference to the substrate 100. For example, in an embodiment, the substrate 200 is a substrate of a photomask. In another embodiment, the substrate 200 is a device substrate (e.g., semiconductor substrate or wafer). The features 202 may be substantially similar to the features 102, also described above with reference to FIG. 1.

Figure 3:
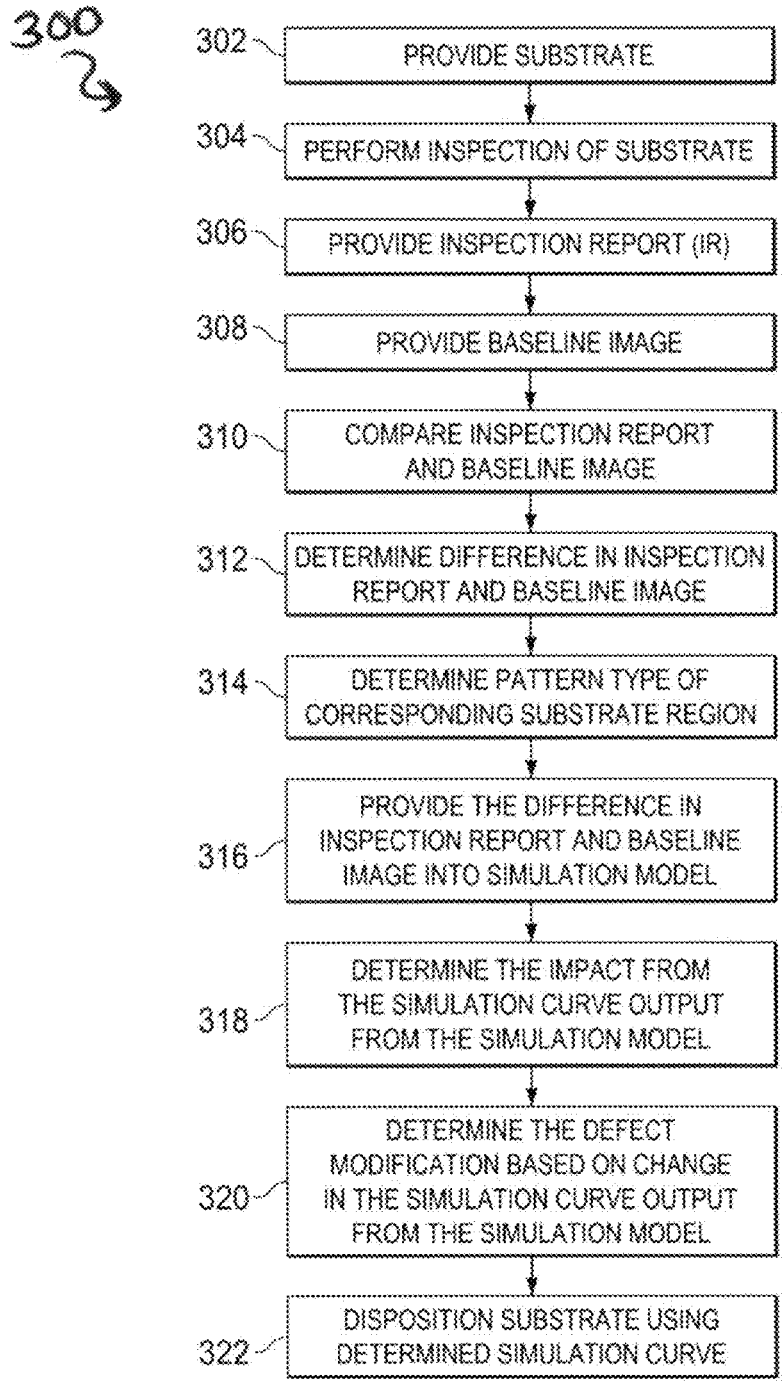
FIG. 3 is a flow chart illustrating an embodiment of a method of identifying and/or characterizing a defect of a substrate.
Figure 4:
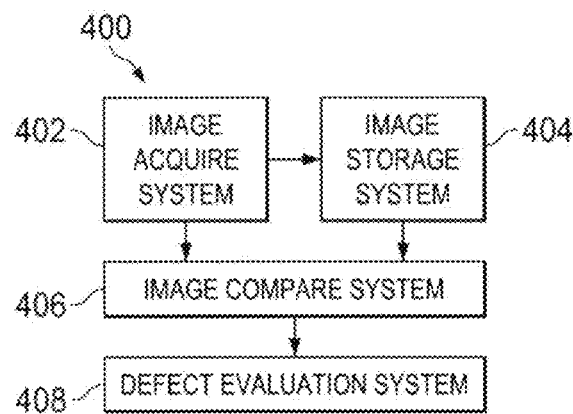
FIG. 4 is a block diagram illustrating an embodiment of a system operable to perform one or more steps of the method of FIG. 3.

Referring now to FIG. 3, illustrated is a method 300 suitable for determining a defect of a substrate used in the fabrication of semiconductor devices. The substrate may be a photomask (e.g., reticle) substrate or a device substrate (e.g., semiconductor substrate) on which one or more semiconductor device(s) are or will-be formed. The method 300 may be used to characterize a defect, for example, determine the existence of a defect, determine the type of defect, determine the impact of a defect (e.g., to performance of the device), and/or the disposition of a substrate having an identified defect. FIG. 4 is illustrative of a system 400; the system 400 may be used to perform one or more of the steps of the method 300.

The method 300 begins at block 302 where a substrate is provided. In an embodiment, the substrate is a photomask or reticle. In such an embodiment, the substrate may be a transparent substrate such as fused silica ($SiO_2$), or quartz, relatively free of defects, calcium fluoride, and/or other suitable material used in a photolithography process. The features formed on the substrate may include attenuating material operable to pattern an incident radiation beam. The attenuating material may include chrome or other materials such as, for example, Au, MoSi, CrN, Mo, $Nb_2O_5$, Ti, Ta, $MoO_3$, MoN, $Cr_2O_3$, TiN, ZrN, $TiO_2$, TaN, $Ta_2O_5$, NbN, $Si_3N_4$, ZrN, $Al_2O_3N$, $Al_2O_3R$, or combinations thereof.

In another embodiment, the substrate provided is a device substrate such as a semiconductor substrate (e.g., wafer). In such an embodiment, the substrate may be a semiconductor substrate that includes an elementary semiconductor including silicon and/or germanium in crystal; a compound semiconductor including silicon carbide, gallium arsenic, gallium phosphide, indium phosphide, indium arsenide, and/or indium antimonide; an alloy semiconductor including SiGe, GaAsP, AlInAs, AlGaAs, GaInAs, GaInP, and/or GaInAsP; or combinations thereof. The substrate may be strained, may be a semiconductor on insulator (SOI), have an epitaxial layer, and/or have other features enhancing performance. The substrate may include any number of semiconductor device features or portions thereof, for example, transistors including gate structures, doped regions such as source/drain regions, diodes including light emitting diode (LED) structures, memory cells, sensors, microelectromechanical systems (MEMS), and the like. The substrate may include any number of layers such as, conductive layers, insulating layers, etch stop layers, capping layers, diffusion/barrier layers, gate layers, hard mask layers, interfacial layers, and/or numerous other suitable layers. Alternatively, although a substrate in the form of a semiconductor wafer may be described; it is to be understood that other examples of substrates and processes may benefit from the present invention such as, for example, printed circuit board substrates, damascene processes, and thin film transistor liquid crystal display (TFT-LCD) substrates and processes.

The method 300 then proceeds to block 304 where an inspection of the substrate is performed. The inspection may include a scan of the substrate to provide an image of the scanned substrate or portion thereof. In an embodiment, an image acquire system 402 is used to perform the inspection scan. The inspection scan system 402 may include a defect review scanning system such as, for example, a scanning electron microscope (SEM), scatterometry analysis tool, an atomic force microscope (AFM), Aerial Image Measurement System (AIMS) from Carl Zeiss Microelectronics Systems (see U.S. Pat. No. 6,268,093, hereby incorporated by reference), DRC technique (see U.S. Pat. No. 6,373,975, hereby incorporated by reference), KLA-Tencor tools, Numerical Technologies, Inc. tools, and/or other systems operate to provide an aerial image of a substrate and its design pattern for example, based on an illumination value.

The inspection of the substrate provided in block 304 produces an inspection report (IR), also referred to as a scan report, provided in block 306 of the method 300. The IR or scan report may be an image of the substrate (or portion thereof) provided by the inspection scan. The image may include all or portion of the substrate, described above with reference to block 302. The image may be a raster graphics image or bitmap. The image may be provided in pseudo color or gray scale (or gray level) bitmap and/or other analysis technique. In an embodiment, the image is a grayscale bitmap image where each pixel is represented by one byte, so that each pixel may correspond to a grayscale value in the range of 0 to 255. The value of the pixel may correspond to the amount of reflection of a radiation source provided to the region corresponding to the pixel.

In an embodiment of the method 300, the inspection report provides an image which much be subsequently converted into a gray level image by light leveling to scale the gray level of the image.

The method 300 then proceeds to block 308 where a baseline image is provided. The baseline image may be an image of a reference substrate and/or other image previously captured and stored. The baseline image may be a raster graphics image or bitmap. The baseline image may be provided in pseudo color or gray scale (or gray level) bitmap and/or other analysis technique. The baseline image may be provided by an inspection of a substrate and provision of an IR substantially as described above with reference to blocks 304 and 306. The substrate that provides the baseline image is described in further detail below.

In an embodiment, the baseline image is an image of the same region (e.g., corresponding to the same coordinates) of the substrate provided at block 302 and scanned at block 304, the baseline image having been captured at an earlier time period. For example, in an embodiment, a baseline image is an image of a photomask previously captured (e.g., days/weeks prior) to the inspection of the substrate described in block 304. For example, the previously captured baseline image may be an image of the photomask at a point in time where any defect of the photomask was determined to be a defect that did not impact the processing of the associated device (e.g., a non-imaging defect) and/or the photomask to be defect-free.

In an embodiment, the baseline image is an image of a device substrate provided in block 302, the baseline image having been captured at an earlier point during the fabrication process than the image captured in block 306. For example, the baseline image of the device substrate may capture the substrate's condition prior to a first process (e.g., an anneal, implant, diffusion, and/or other process forming a feature on the substrate), while the IR image of block 306 captures the condition of the substrate after the first process is completed on the substrate. Thus, in an embodiment, the baseline image is an image of a device substrate previously captured (e.g., hours/days/weeks prior) to the inspection of the substrate described in block 304.

In an embodiment, the baseline image is an image of a device substrate, different than the device substrate provided in block 302 of the method 300. For example, the baseline image may be an image of a device substrate having the same pattern-type formed thereon and the image corresponding to the same coordinates of the substrate. The baseline image may be a reference image, for example, of a substrate known to have provided a suitable device.

Referring to the exemplary system 400, the baseline image may be acquired by the image acquire system 402 and stored in an image storage system 404. The image storage system 404 may include an information handling system such as the information handling system 2700, described below with reference to FIG. 27.

The method 300 then proceeds to block 310 where a comparison is performed between the IR image and the baseline image to determine a difference. The comparison of the IR image and the baseline image may provide to indicate a presence of a defect in the IR image and its corresponding substrate as described in block 312.

The comparison between images may be performed in various ways. For example, the images may be provided in gray scale, pseudo color, and/or other raster forms. The comparison may be performed by manual inspection, or by a system designed to analyze differences in color and/or gray scale between the two images. In an embodiment, the images to be compared are provided as grayscale images and the baseline gray-level subtracted from the gray-level of the image provided in block 306 to determine a "difference". See, U.S. patent application Ser. No. 11/747,150, which is hereby incorporated by reference in its entirety. Block 310 may be performed by an image compare system 406 of FIG. 4. The image compare system 406 may include a computer readable medium that includes instructions for performing the steps of the method 300 described herein. One example of the image compare system 406 is the information handling system 2700, described below with reference to FIG. 27.

Figure 5:
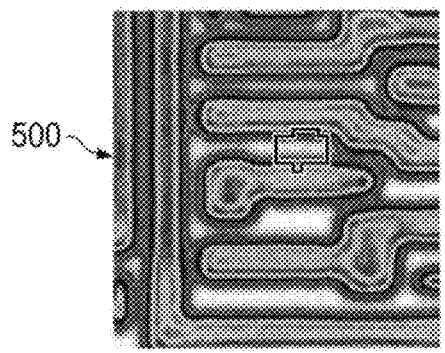
FIGS. 5, 6a, 6b, and 6c are embodiments of pseudo-color images provided by a scan of a substrate.
Figure 6A:
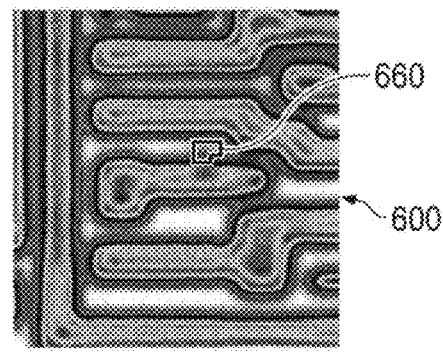
Figure 6B:
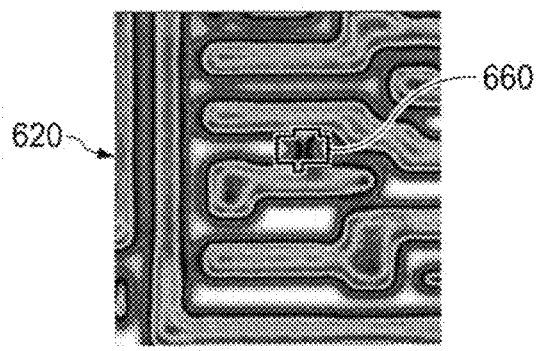
Figure 6C:
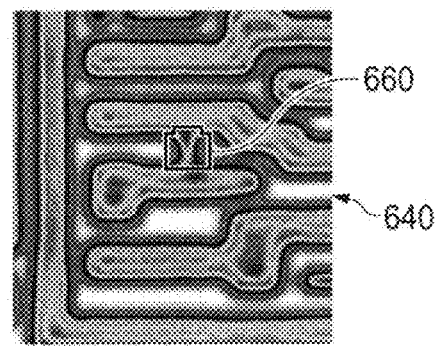

Referring to the examples of FIGS. 5 and 6a, 6b, and 6c illustrated are a plurality of images such as provided by an IR. FIG. 5 illustrates a pseudo color image 500 that provides an embodiment of a baseline image of a substrate. FIGS. 6a, 6b, and 6c provide pseudo color images 600, 620, and 640 respectively. In an embodiment, images 600, 620 and 640 are each provided of the same substrate at different points in time. For example, the image 600 may be an image of a photomask substrate at day n; the image 620 may be an image of a photomask substrate at day n+1; the image 600 may be an image of a photomask substrate at day n+2. However, any displacement in time may be possible. The image 500 may be the baseline image of the same substrate as illustrated in the images 600, 620, and 640. In another embodiment, the image 500 is a baseline image of a different substrate having the same pattern formed thereon. The images 600, 620, and 640 illustrate the development of a defect 660. The defect 660 may be increasing in size over time, e.g., increasing with each image 600, 620, 640.

The method 300 then proceeds to block 312 where a difference between an IR report image provided in block 306 and the baseline image provided in block 308 is determined. As illustrated above, the comparison of the IR image and a baseline image may be performed in various ways. The images may be provided in gray scale, pseudo color, and/or other raster forms. The comparison may be performed by manual inspection, or by a system designed to analyze differences in color and/or gray scale between the two images.

In an embodiment, the IR image and the baseline image are provided as grayscale images. The baseline gray-level may then be subtracted from the corresponding gray-level of the IR image to determine a "difference". U.S. patent application Ser. No. 11/747,150, which is hereby incorporated by reference in its entirety, describes this comparison in further detail. The image comparison may be performed by an image comparison system 406 that may include a computer readable medium that includes instructions for performing the steps of the method 300 and/or the method 1200 described below. One example of an image comparison system 406 is the information handling system 2700, described below with reference to FIG. 27.

FIG. 12 illustrates an embodiment of a method 1200 that provides for a difference in a baseline and IR image. The method 1200 begins at block 1202 where an IR image and baseline image are provided. The IR image and baseline image may be provided as grayscale images for example, a grayscale bitmap. The method 1200 then proceeds to block 1204 where the baseline and IR images are aligned such that the same point on the respective substrate is aligned at the same coordinate on the image. The method 1200 then proceeds to block 1206 where a first value of a first coordinate on the IR image is determined. In an embodiment, the first value is a grayscale value, such as a value between 0 and 255. In block 1208, a second value of the same first coordinate on the baseline image is determined, again for example, a grayscale value between 0 and 255. It is noted that the values may be determined on a pixel by pixel basis, a matrix of pixels (e.g., 3×3, 5×5), and/or other predefined region of the image (e.g., such as by averaging the values of a region). The method 1200 then proceeds to block 1210 where the difference in the first and second values is determined. In an embodiment, the difference is provided as an absolute value. The difference is then stored in a memory component in block 1212, for example, a component such as storage 2706 of the information handling system 2700 illustrated in FIG. 27. The difference may be stored and/or represented as a value on a grayscale image, such as the gray-level differential images described below. The method 1200 may return to block 1206 to continue to select coordinates on the images until any or all of the images are considered.

Figure 7A:
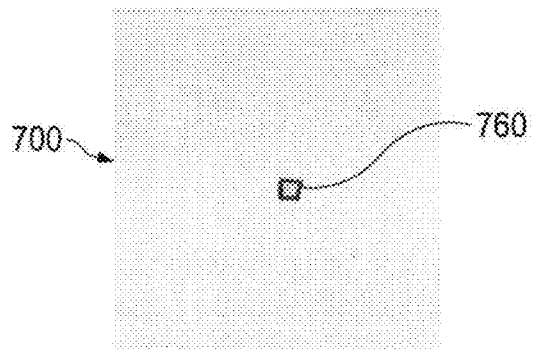
FIGS. 7a, 7b, and 7c are embodiments of gray-level difference images generated from scan images of a substrate with respect to a baseline image.
Figure 7B:
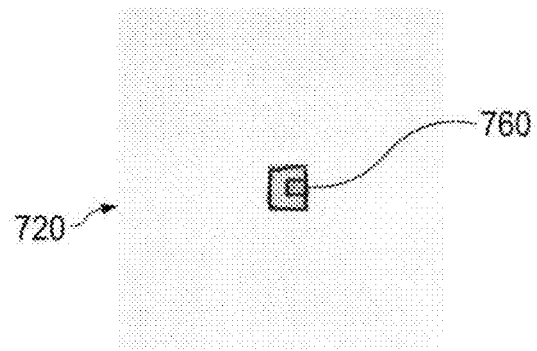
Figure 7C:
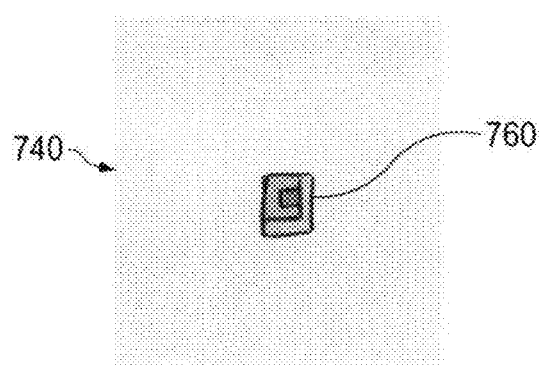

Referring to the example of FIGS. 7a, 7b, and 7c, illustrated are gray-level differential images 700, 720, and 740 respectively. The gray-level differential images 700, 720, and 740 describe differences in grayscale images provided, for example by the subtraction of the gray-level of a baseline image from an IR image. For example, the gray-level differential images 700, 720, and 740 may be the resultant image in a grayscale bitmap where a difference in pixel value between a baseline image and another image is represented. In an embodiment, the value of the pixel in the gray-level differential images 700, 720, and 740 is the absolute value of a difference of a pixel (at the same coordinates of the substrate) of a baseline image and the IR image. Thus, the gray-level differential images 700, 720, and 740 have marks or indications at the regions 760 of the substrate where there is a difference between the images (and thus, the substrates represented by the images). The regions 760 may be indicative of a defect on the IR image where no "defect" is present on the baseline image.

In an embodiment, the gray-level differential image 700 represents a difference between the image 600 and the baseline image 500, described above with reference to FIGS. 6a and 5 respectively. In an embodiment, the gray-level differential image 720 represents a difference between the image 620 and the baseline image 500, described above with reference to FIGS. 6b and 5 respectively. In an embodiment, the gray-level differential image 700 represents a difference between the image 640 and the baseline image 500, described above with reference to FIGS. 6c and 5 respectively.

The method 300 then proceeds to block 314 where a pattern type of the substrate is determined. The pattern type determined may be the pattern that is provided in the corresponding region of the substrate where a difference in the IR and baseline image was identified in block 312. The pattern type may be a line/space pattern, a contact pattern (e.g., contact hole), a dot pattern, an optical proximity correction (OPC) pattern, and/or other suitable pattern types.

The method 300 then proceeds to block 316 where the determined difference between the IR image and the baseline image is provided to a simulation model. The simulation model may be directed to the pattern type determined in block 314. For example, the simulation model may be pattern-type specific. The simulation model may provide an indication of type of defect, degree (e.g., severity) of defect, and/or the effect of the defect represented by the determined difference between the IR image and the baseline image.

Figure 8:
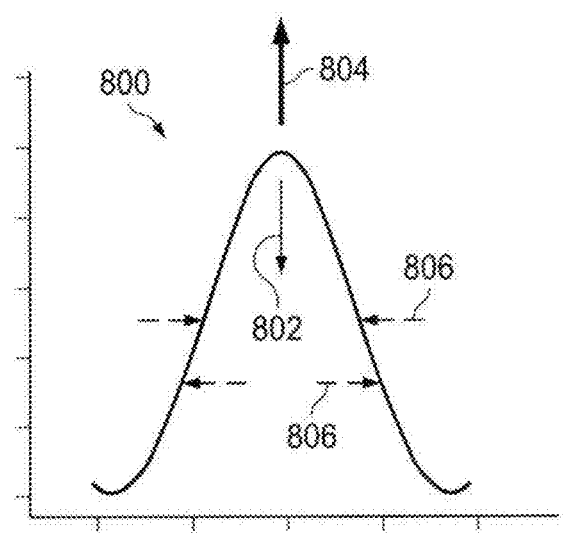
FIG. 8 illustrates an embodiment of a simulation curve output from a simulation model according to one or more aspects of the present disclosure.

In an embodiment, the simulation, which is discussed in greater detail below, provides as an output a curve that represents the characteristics of the defect defined by the difference in baseline and IR images. FIG. 8 is illustrative of a simulation curve 800 provided for a determined difference between the IR image and the baseline image. The simulation curve 800 may be output from a simulation having an input of a difference between an IR image and a baseline image. The x-axis of the simulation curve 800 may provide a relative position on an image or corresponding substrate. In an embodiment, the y-axis of the simulation cure 800 provides a relative intensity of energy, for example, determined by the scans. For example, the y-axis may be a relative intensity of energy provided a scan incident a photomask substrate. The characteristics of the curve 800 may provide an indication of the type of defect, severity of a defect, and/or the effect of the defect of an associated device. For example, in an embodiment, a photosensitive material energy gap may be provided at a value on the y-axis thus, a curve extending above the photosensitive material energy gap may cause the defect to provide an undesired image on the photosensitive material. As a further example, for a curve 800 representing a pin-hole defect, a shielding effect may lower the energy curve from an expected profile, illustrated by 802. As another example, for a curve 800 representing a pin dot defect, high illumination may lift the energy curve above an expected profile, illustrated by 804. Different loading effects of a line pattern and the associated proximity effects may cause the curve to shrink or extend, illustrated by 806. In other embodiments, the shape of the curve 800 may be altered (e.g., for OPC or reticle enhancement technique (RET) features). Thus, inspection of the simulation curve such as simulation curve 800 may be illustrative of the type of defect, size of defect, and/or effect of the device.

Figure 11:
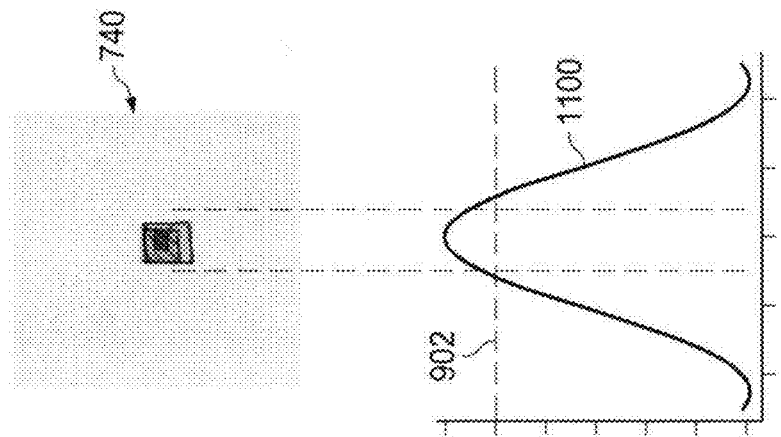
FIGS. 9, 10, and 11 are embodiments of simulation curves and the associate gray-level difference image generated according to one or more aspects of the present disclosure.
Figure 10:
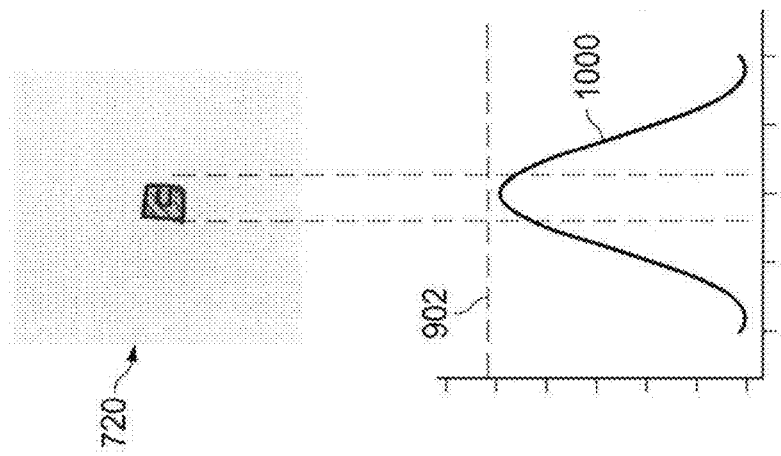
Figure 9:
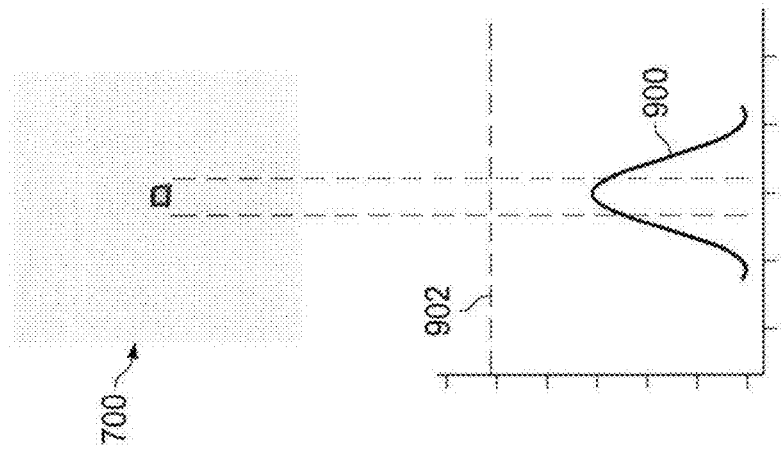

Referring now to FIGS. 9, 10, and 11, illustrated are simulation results, specifically simulation curves 900, 1000, and 1100. The simulation curves 900, 1000, and 1100 may include an x-axis of distance (e.g., coordinate) of an image or associated substrate and a y-axis of a relative intensity or gray-scale value. The simulation curve 900 is representative of the simulation result of the gray-level differential image 700, described above with reference to FIG. 7a. The simulation curve 1000 is representative of the simulation result of the gray-level differential image 720. The simulation curve 1100 is representative of the simulation result of the gray-level differential image 740. The simulation curve 1100 illustrates that the curve extends above a photosensitive material active energy gap line 902. Thus, the defect defined by the gray-level differential image 740 may, undesirably, print onto the wafer. It is noted that the curve and/or the active energy gap line 902 may be modified by altering the process light source, material (e.g., photosensitive material), and/or other factors that affect the photosensitive material active energy gap.

Turning now to the simulation model of block 316, FIG. 13 illustrates an embodiment of a method 1300 of generating a simulation model such as the model used in block 316 of the method 300. In an embodiment, the simulation model is directed to characterizing defects of a device substrate such as a semiconductor wafer. In such an embodiment, the simulation model may be generated from wafer finite element model (FEM) data. In another embodiment, the simulation model is directed to characterizing defects of a photomask substrate. In such an embodiment, the simulation model may be generated from aerial image data. The method 1300 illustrates an embodiment of a method of providing a simulation model that produces simulation output curves such as described with reference to FIGS. 8, 9, 10 and/or 11.

The method 1300 begins at block 1302 where a scan report of a reference substrate is received. In an embodiment, the scan report is provided for a photomask and the scan report generated by an Aerial Image Measurement System (AIMS) from Carl Zeiss Microelectronics Systems. However, other systems are possible and within the scope of the present disclosure. In an embodiment, the scan report includes FEM data of a device substrate. In an embodiment, the reference substrate is a substrate that includes no or substantially no defects, and/or includes known or well-characterized defects. Thus, the reference scan report may be considered a "good" or verified report of a "good" or verified substrate.

Figure 14:
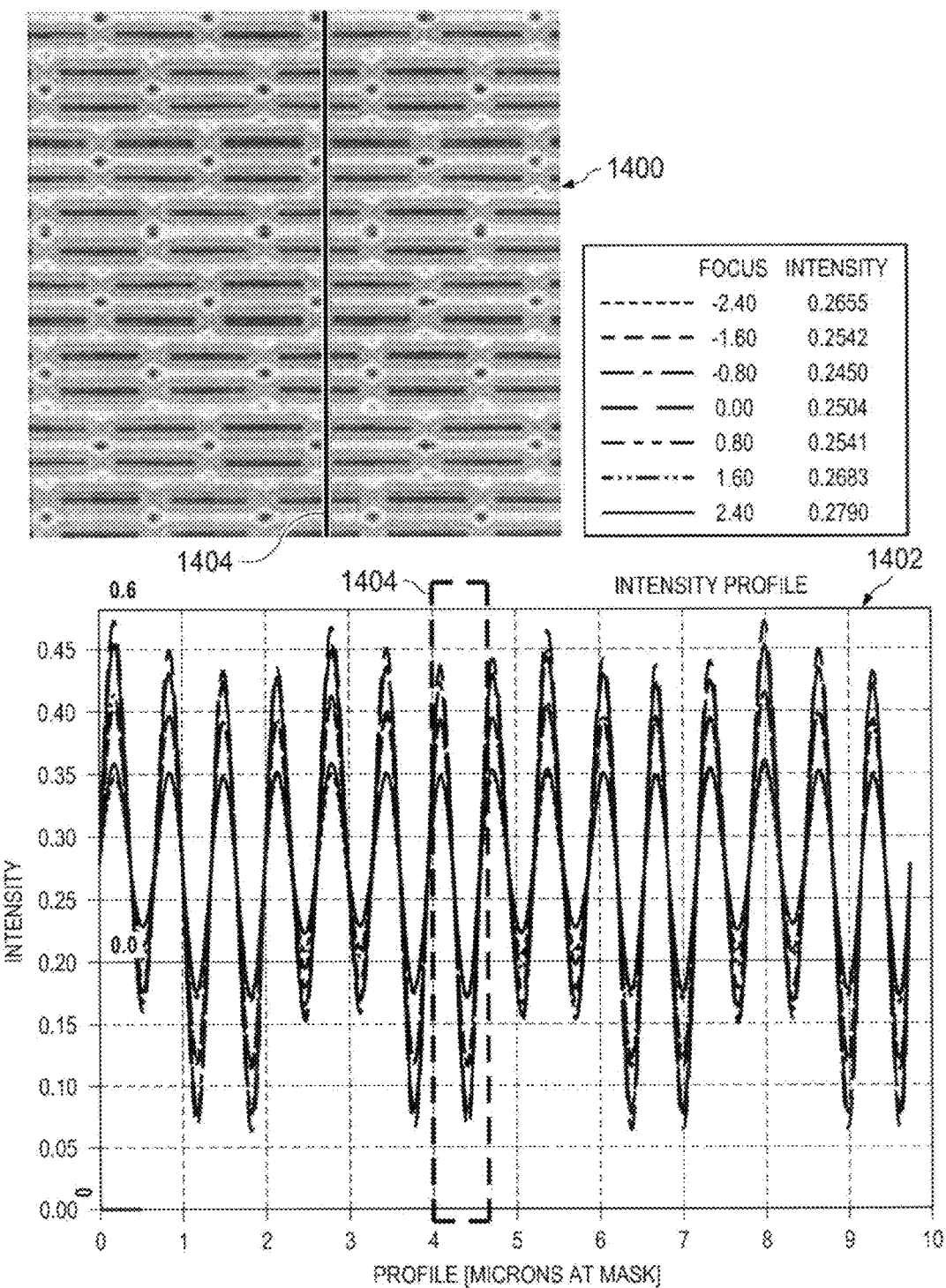
FIGS. 14, 15, 16, and 17 are embodiments of images of a substrate and corresponding data or intensity profile.

Referring to the example of FIG. 14, illustrated is an image 1400 of a reference substrate. The image 1400 may be provided by a scan of a reference substrate such as discussed with reference to block 1302. FIG. 14 also illustrates the corresponding intensity profile (e.g., AIMS intensity profile) 1402. The intensity profile 1402 includes an x-axis providing for the profile location (e.g., in microns) and a y-axis of intensity. The corresponding intensity profile of position 1404 on the substrate or image thereof is illustrated.

Figure 16:
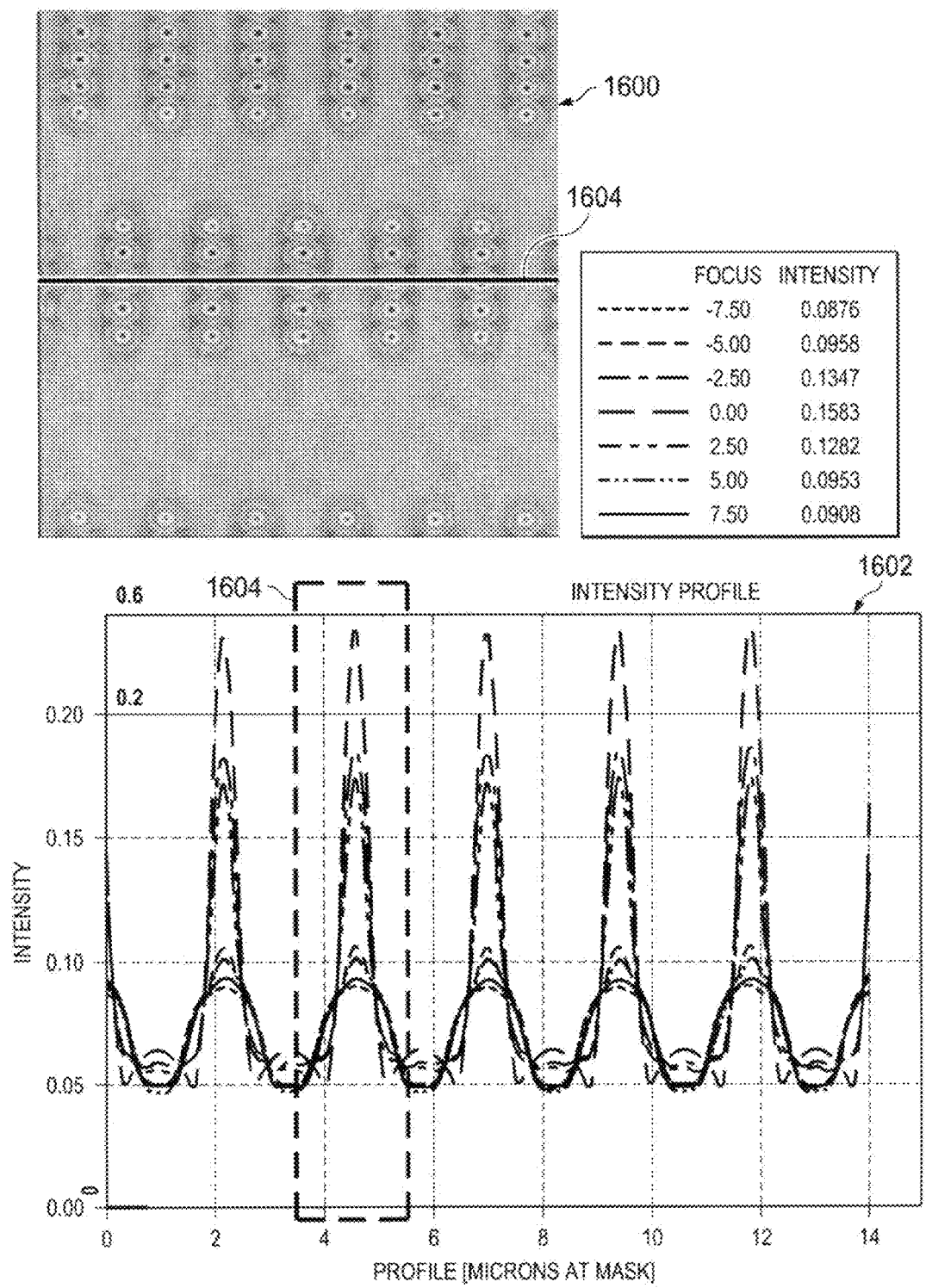

Referring to the example of FIG. 16, illustrated is an image 1600 of a reference substrate. The image 1600 may be provided by a scan of a reference substrate such as discussed with reference to block 1302. FIG. 16 also illustrates the corresponding intensity profile (e.g., AIMS intensity profile) 1602. The intensity profile 1602 includes an x-axis providing for the profile location (e.g., in microns) and a y-axis of intensity. The corresponding intensity profile of position 1604 on the substrate or image thereof is illustrated.

The method 1300 proceeds to block 1304 where a scan report of a defect substrate is received. In an embodiment, the scan report is generated by scanning a photomask such as by an Aerial Image Measurement System (AIMS) from Carl Zeiss Microelectronics Systems. However, other systems are possible and within the scope of the present disclosure. In an embodiment, the scan report includes FEM data of a device substrate. In an embodiment, the defect substrate is a substrate that includes at least one defect. The at least one defect may be identified and/or characterized before, after or by the scan. The defect substrate may be the reference substrate at a later point in time (e.g., after +x days).

Figure 15:
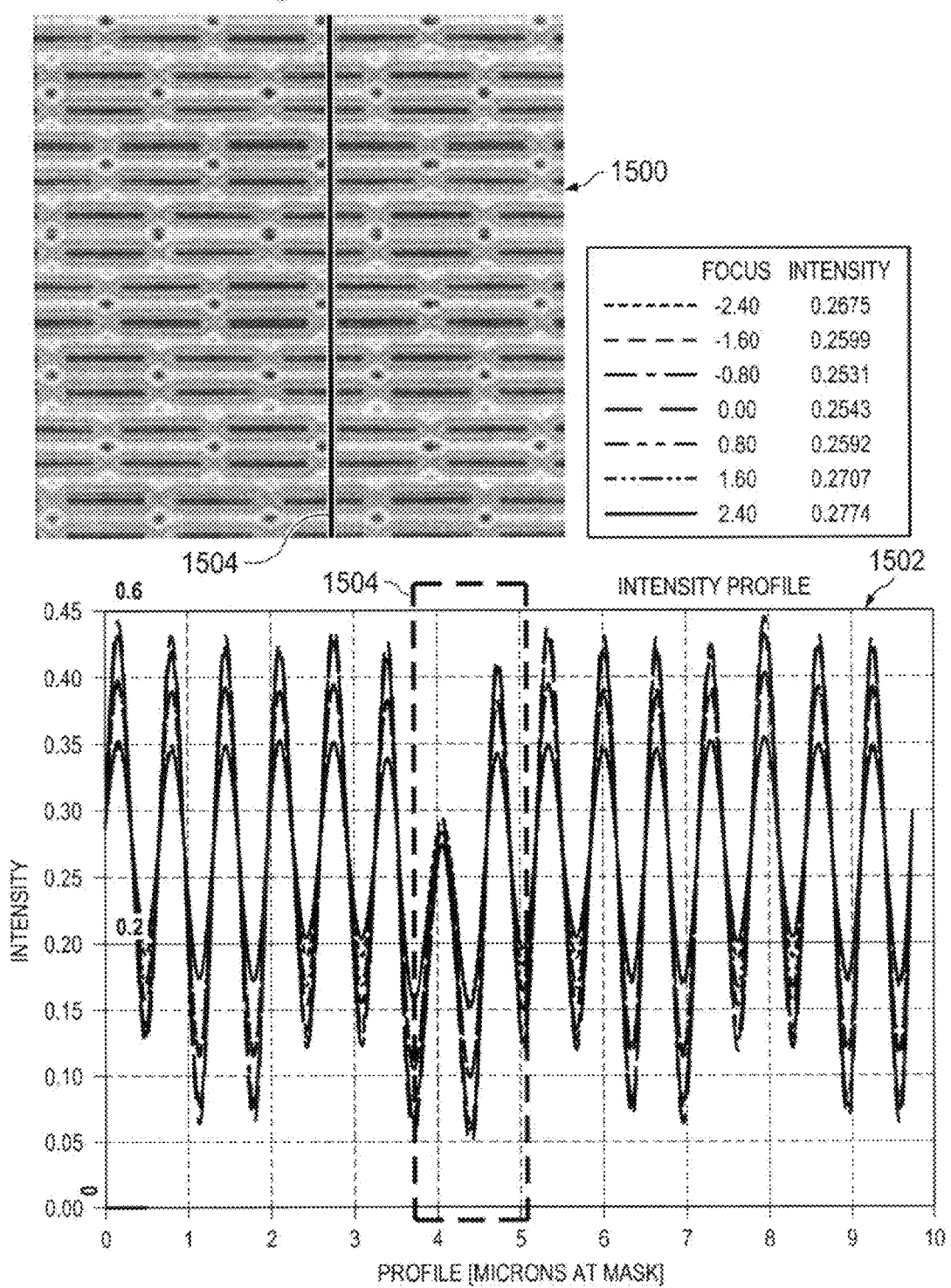

Referring to the example of FIG. 15, illustrated is an image 1500 of a defect substrate. The image 1500 may be provided by a scan of a defect substrate such as discussed with reference to block 1304. FIG. 15 also illustrates the corresponding intensity profile (e.g., AIMS intensity profile) 1502. The intensity profile 1502 includes an x-axis providing for the profile location (e.g., in microns) and a y-axis of intensity. The corresponding intensity profile of position 1504 of the substrate is also indicated on the image 1500 is illustrated. Position 1504 illustrates the presence of a defect. In the illustrated embodiment, the defect is a line-space defect. It is noted that FIGS. 14 and 15 are provided of the same pattern-type and thus, may be used to establish a simulation model as described below.

Figure 17:
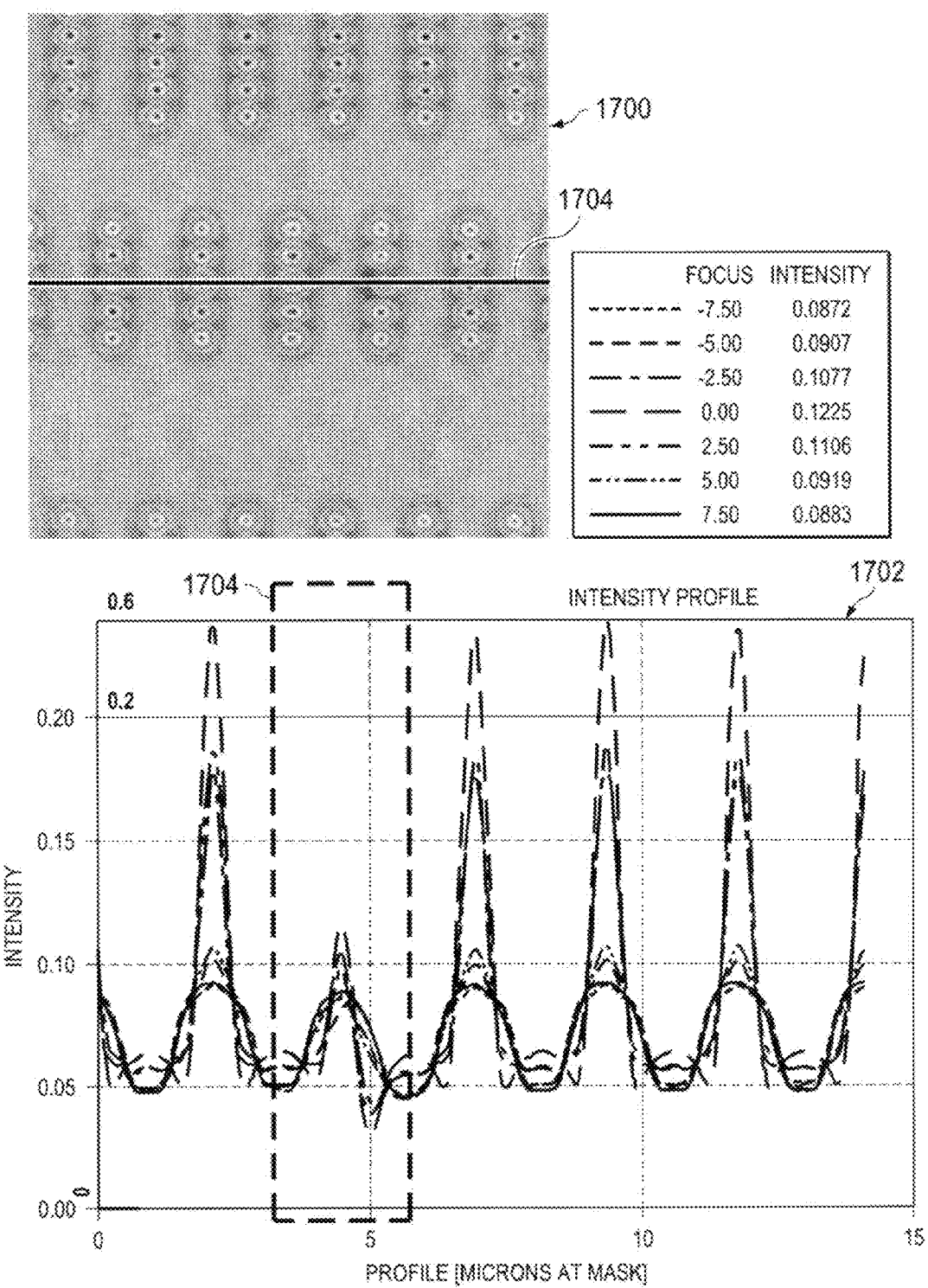

Referring to the example of FIG. 17, illustrated is an image 1700 of a defect substrate. The image 1700 may be provided by a scan of a defect substrate such as discussed with reference to block 1304. FIG. 17 also illustrates the corresponding intensity profile (e.g., AIMS intensity profile) 1702. The intensity profile 1702 includes an x-axis providing for the profile location (e.g., in microns) and a y-axis of intensity. The corresponding intensity profile of position 1704 of the substrate is also indicated on the image 1700 is illustrated. Position 1704 illustrates the presence of a defect. In the illustrated embodiment, the defect is a pin-hole defect. It is noted that FIGS. 16 and 17 are provided of the same pattern-type and thus, may be used to establish a simulation model as described below.

The method 1300 then proceeds to block 1306 where the defect signature provided by the scan report of the defect substrate is determined and stored. The defect signature may be determined and/or stored by an information handling system such as the information handling system 2700, described below with reference to FIG. 27. In an embodiment, the defect signature is specific to a type of pattern formed on the substrate. The defect signature may include a determination of whether a defect of a photomask will print onto a photosensitive layer during a lithography process. In an embodiment, the defect signature is as illustrated in region 1704 of the profile 1702. In an embodiment, the defect signature is as illustrated in region 1504 of the profile 1502.

In an embodiment, the method 1300 then proceeds back to block 1304 where an additional scan of a defect substrate is performed. The scan may be of the same defect substrate at a later point in time (e.g., the defect having changed in character) and/or a different defect substrate. Blocks 1304 and 1306 are repeated until a sufficient quantity of data is provided to develop the simulation model in block 1308. The simulation model may be particular to a substrate type and/or a pattern-type (e.g., the type of pattern formed on the region of the substrate). In an embodiment, the simulation model uses the defect signature data to provide a system operable to provide a characterization (e.g., type, size, affect) of an unknown defect based on the database of defect signatures provided by blocks 1304 and 1306.

Thus, the method 1300 provides for development of a simulation model by the collection and storage of a plurality of defect signatures, for example, for a specific substrate type and/or pattern type. The simulation model may correlate an image of a patterned substrate with an intensity profile of the pattern, including a defect in the pattern. The simulation model may be continually updated based on additional information provided by a scan of a defect substrate. The correlation of an image of a patterned substrate with an intensity profile provided by the simulation model provides for an input of an image into the simulation model and an output of a simulation curve, such as described above with reference to FIGS. 8-11.

Referring again to FIG. 3, from the simulation output, the method 300 proceeds to block 318 where the impact or effect on the processing and resultant device(s) is determined from the simulation output. As discussed above, in an embodiment, the simulation output illustrates whether a defect of a photomask will provide an image onto a photosensitive layer. In an embodiment, the simulation output illustrates a type of defect based on the shape of the simulation curve.

The method 300 also illustrates block 320 which determines from the simulation output what the magnitude of change in the defect (e.g., size) may be. For example, in an embodiment a resultant simulation curve may be compared to a previously generated simulation curve for example, based upon an earlier generated IR image. For example, a simulation curve generated from an IR image taken a day n of a substrate may be compared with a simulation curve generated from an IR image taken at a day n-x of a substrate.

The method 300 then proceeds to block 322 where the substrate is dispositioned based on the result of the simulation. The disposition may include to clean the substrate, repair the substrate, rework the substrate, re-tool the substrate, scrap the substrate, and/or proceed with processing.

Figure 18:
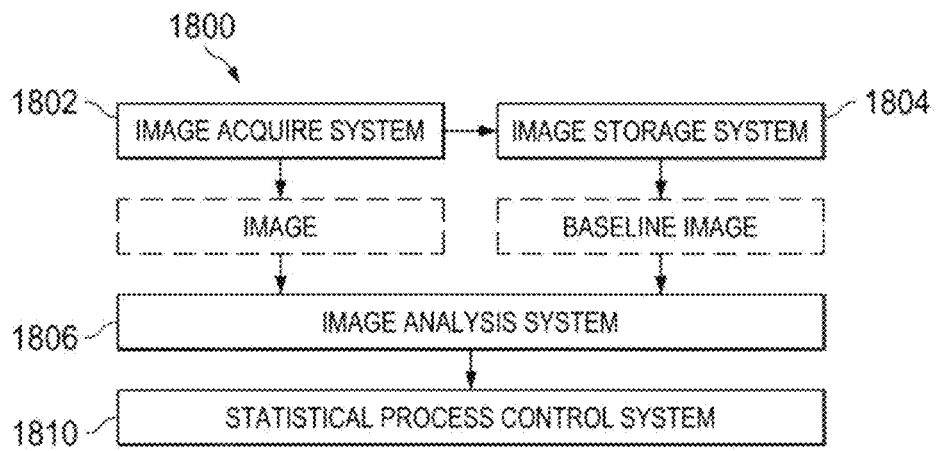
FIG. 18 is a block diagram of a system operable to perform the analysis of a scan report according to one or more aspects of the method of FIG. 19.
Figure 19:
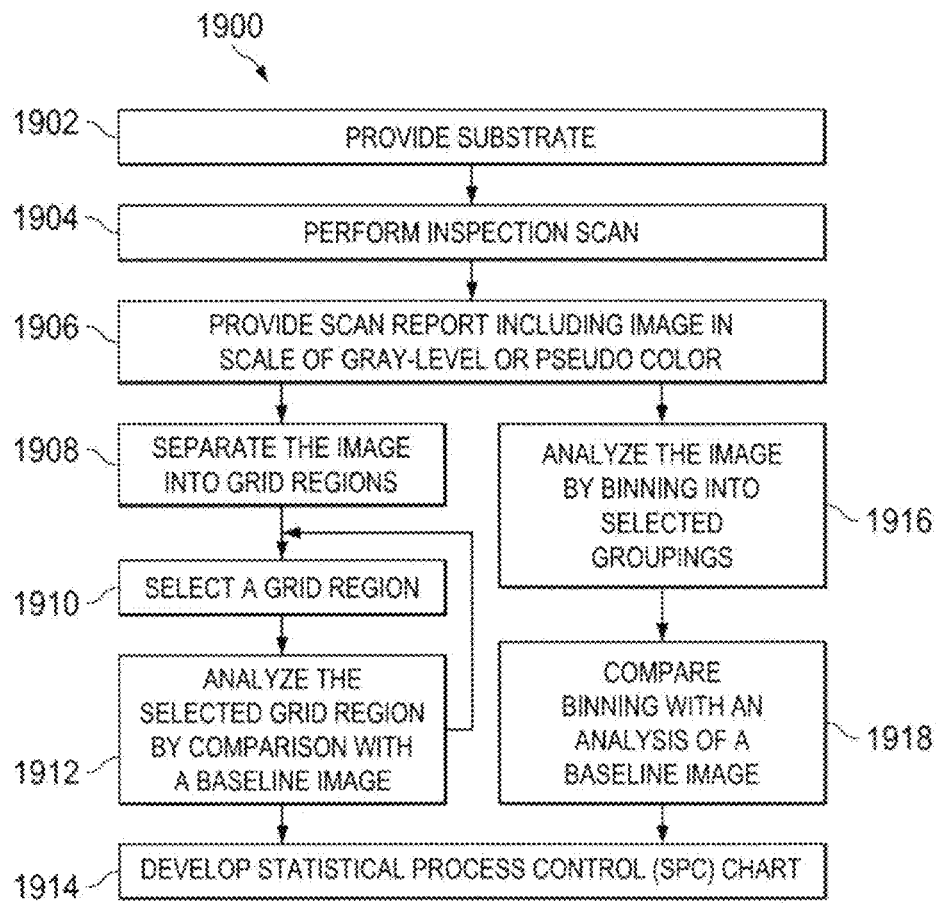
FIG. 19 is a flow chart of an embodiment of a method of analyzing a scan report according to one or more aspects of the present disclosure.

Referring now to FIGS. 18 and 19, illustrated is a method 1900 of analyzing and monitoring defects of a substrate used in semiconductor device fabrication; a system 1800 may be used to perform one or more of the steps of the method 1900. The method begins at block 1902 where a substrate is provided. The substrate may be a photomask (also referred to as a "reticle") or a semiconductor device substrate. Example photomask substrates include transparent substrates such as fused silica ($SiO_2$), quartz, calcium fluoride, or other suitable material. Exemplary semiconductor device substrates include silicon in crystalline structure, germanium, compound semiconductors such as, silicon carbide, gallium arsenide, indium arsenide, and/or indium phosphide. Other exemplary substrates include those suitable for thin film transistor liquid crystal display (TFT-LCD) substrates and processes.

The substrate may have one or more features formed thereon. The features may include a pattern defining a portion of a semiconductor device such as an integrated circuit, LED, sensor device, and/or other relevant functionality.

The method 1900 then proceeds to block 1904 an inspection scan is performed. In an embodiment, an image acquire system 1802 is used to perform the inspection scan. The image acquire system 1802 may be substantially similar to the image acquire system 402, described above with reference to FIG. 4. The inspection scan may include a defect review scanning system such as, for example, a scanning electron microscope (SEM), an atomic force microscope (AFM), Aerial Image Measurement System (AIMS) from Carl Zeiss Microelectronics Systems (see U.S. Pat. No. 6,268,093, hereby incorporated by reference), DRC technique (see U.S. Pat. No. 6,373,975, hereby incorporated by reference), KLA-Tencor tools, Numerical Technologies, Inc. tools, and/or other systems operate to provide an aerial image of a substrate and its design pattern based on an illumination value.

The method 1900 then proceeds to block 1906 where a scan report is provided. The scan report may be an image of the substrate provided by the inspection scan. The image may include all or portion of the substrate, described above with reference to block 1902. The image may be a raster graphics image or bitmap. The image may be provided in pseudo color or gray scale (or gray level) bitmap and/or other analysis technique. In an embodiment, the image is a grayscale bitmap image where each pixel is represented by one byte, so that each pixel may correspond to a grayscale value for example in the range of 0 to 255. The value of the pixel may correspond to the amount of reflection of a radiation source provided to the region corresponding to the pixel.

Figure 20:
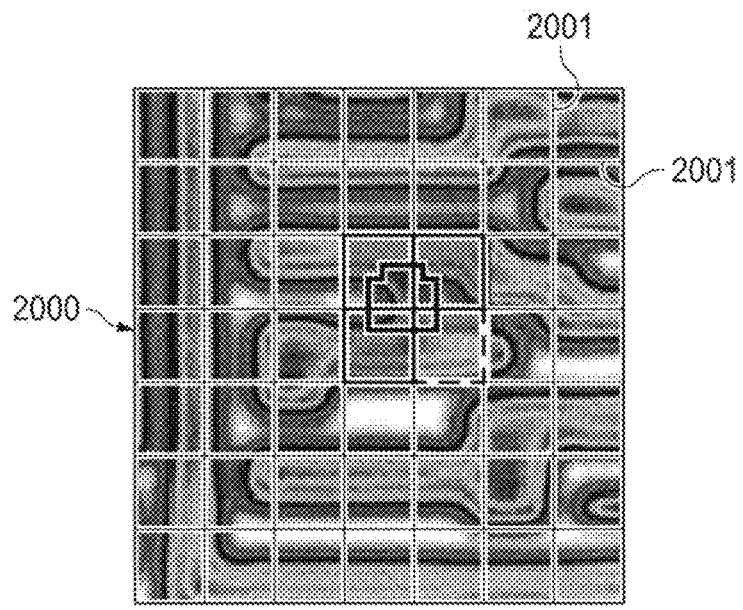
FIG. 20 is illustrative of an embodiment of an image provided by a scan report of a substrate according to one or more aspects of the present disclosure.

In an embodiment, after the provision of the scan report, the method 1900 proceeds to block 1908 where the image of the scan report is divided into a plurality of regions. The plurality of regions may be referred to as providing a grid or a grid view of the image with each grid defining a region. Referring to the example of FIG. 20, an image 2000 is provided having a plurality of regions or grid regions 2002 designated. Any plurality of grid regions may be designated on the image from the scan report or a portion of the image from the scan report. The grid regions may be regular in shape or irregular in shape. Each of the grid regions may include any number of pixels.

The method 1900 then proceeds to block 1910 where one region of the plurality of grid regions designated in block 1908 is selected. The region may be selected based upon criticality of the region in the design of the associated device, the criticality of region in the manufacturing of the associated device, desire for engineering analysis of the selected region, and/or other purposes for analysis.

Figure 21:
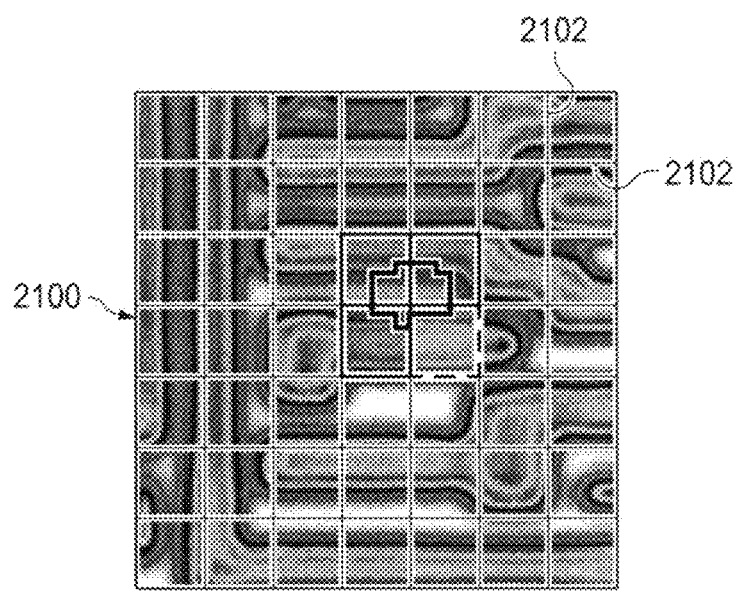
FIG. 21 is illustrative of an embodiment of an image provided by a scan report of a baseline substrate according to one or more aspects of the present disclosure.

The method 1900 then proceeds to block 1912 where an image of the selected grid region is analyzed compared to a baseline image. In an embodiment, a baseline image is an image of the same region (e.g., corresponding to the same coordinates) of the substrate at an earlier time period. For example, in an embodiment, an image of a selected region (e.g., a selected grid region) of a photomask is compared to a previously captured image of the same selected grid region of the photomask. The previously captured image may be an image of the photomask at a point in time where any defect of the photomask was determined to be a defect that did not impact the processing of the associated device (e.g., a non-imaging defect) and/or the photomask was determined to be defect-free. As another example, in an embodiment, an image of a selected region (e.g., grid region) of a device substrate (e.g., semiconductor substrate) is compared to an image of the substrate previously captured during the fabrication process. For example, the image of the device substrate may be compared prior to and after a process such as, for example, an anneal, implant, diffusion, and/or other process forming a feature on the substrate. As yet another example, in an embodiment, an image of a selected region (e.g., grid region) of a device substrate is compared to a baseline image of a different device substrate having the same pattern formed thereon and corresponding to the same coordinates. The comparison image may be a baseline or reference substrate, for example, known to provide a suitable device. An example of an image of a baseline or reference substrate 2100 is provided in FIG. 21. The baseline image 2100 may be an image of a substrate at substantially the same region (i.e., coordinates) as the image 2000 of FIG. 20. The baseline image 2100 may also be designated as including grid regions 2102. The grid regions 2100 may be substantially the same in coordinates as the grid regions 2001, describe with reference to FIG. 20.

The comparison of the grid region on the image provided by the method 1900 and a baseline image may be performed in various ways. For example, the images may be provided in gray scale, pseudo color, and/or other raster forms. The comparison may be performed by manual inspection, or by a system designed to analyze differences in color and/or gray scale between the two images. The comparison may include binning the colors and/or gray levels of image provided by the scan of block 1906 and the corresponding baseline image, and then comparing the binning results between the two images. Binning the colors and gray levels is discussed in further detail below. In an embodiment, the images are provided as grayscale images and the baseline gray-level subtracted from the gray-level of the image of the selected grid region to determine a "difference." See, U.S. patent application Ser. No. 11/747,150, which is hereby incorporated by reference in its entirety. It is noted that the comparison of the image 2000 and the image 2100 illustrates that the image 2000 includes a defect 2004 in its pattern (e.g., a variation in the image 2000 from the baseline image 2100). Blocks 1908, 1910, and/or 1912 may be performed by an image analysis system 1806 of FIG. 18. The image analysis system 1806 may include a computer readable medium that includes instructions for performing the steps of the method 1900. One example of an image analysis system 1806 is the information handling system 2700, described below with reference to FIG. 27.

The blocks 1910 and 1912 may be repeated any number of times. For example, any number of the plurality of designated grid regions may be selected for comparison with a corresponding baseline image.

Figure 26:
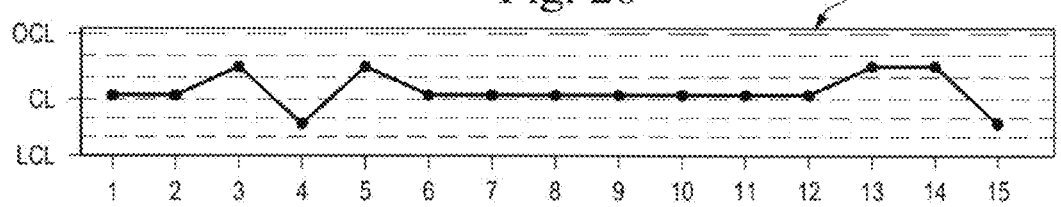
FIG. 26 illustrates an embodiment of a statistical process control (SPC) chart.

The method 1900 then proceeds to block 1914 where the comparison of the selected grid region image and the corresponding baseline image may be tracked by a statistical process control (SPC) chart. The SPC chart may be used to monitor the quality of the substrate based on differences (e.g., in color or gray-value) from its baseline image. The SPC chart may be provided for a selected grid, or a plurality of grids. An exemplary SPC chart 2600 is illustrated in FIG. 26. The SPC chart 2600 includes a target or mean value (CL), an upper control limit (UCL), and a lower control limit (LCL). The tracked variable may include a variable representing a difference in the binning between the grid region and the baseline image, a gray level difference between the grid region and the baseline image (as discussed above), and/or other suitable output. In an embodiment, block 1914 is omitted from the grid-level comparison. The SPC chart may be generated by an SPC system typical of a semiconductor fabrication process control. Referring the example of FIG. 18, an SPC system 1810 is illustrated. One example of the SPC system 1810 is the information handling system 2700, described below with reference to FIG. 27.

In an embodiment of the method 1900, after the provision of the scan report, the method 1900 (also or alternatively) proceeds to block 1916 where the image of the scan report, or portion thereof, is analyzed by binning the information of the image into selected groupings. The binning may include determining the number of counts or occurrences of a given value in the image. For example, a pseudo color image may be analyzed and the occurrence of each of the plurality of colors may be determined. As another example, a grayscale image may be analyzed and the occurrence of various values determined.

Figure 22:
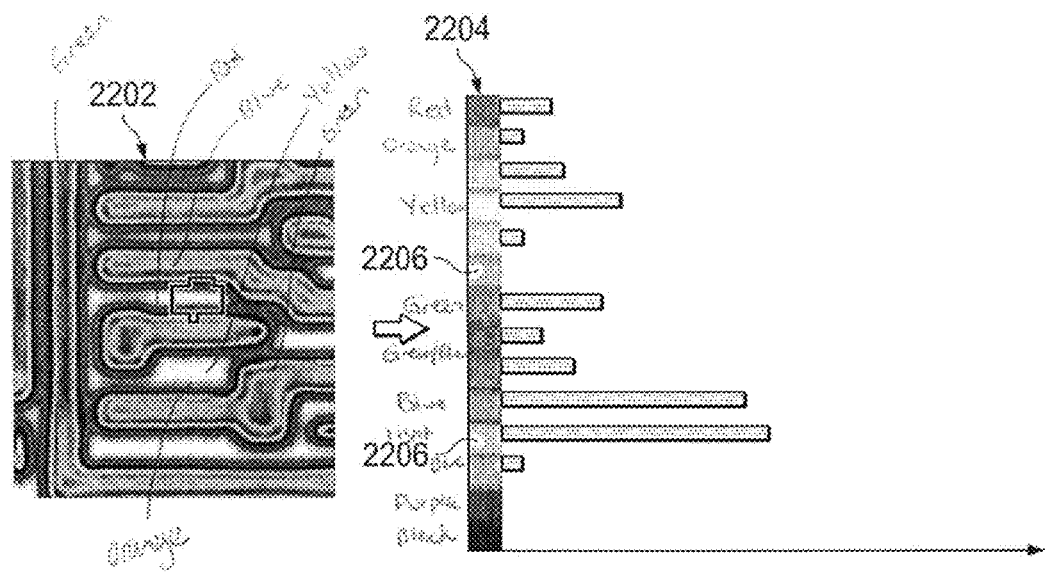
FIGS. 22-25 are illustrative of embodiments of images provided by a scan report of a substrate and a corresponding binning result according to one or more aspects of the present disclosure.

FIG. 22 is illustrative and includes a pseudo color image 2202 and an associated binning result 2204 indicating the occurrence (count) of each color-type 2206 within the image (or designated portion thereof). The occurrence of a color-type may be quantified by a single pixel, a plurality of pixels (e.g., a 3×3 grouping of pixels), and/or other selected sized area of the image. For example, in an embodiment, a single pixel color is determined and added as one count for the color-type 2206. In another embodiment, a color of a group of pixels (or majority color of the group of pixels) is determined and one count for the associated color-type 2206 provided.

Figure 23:
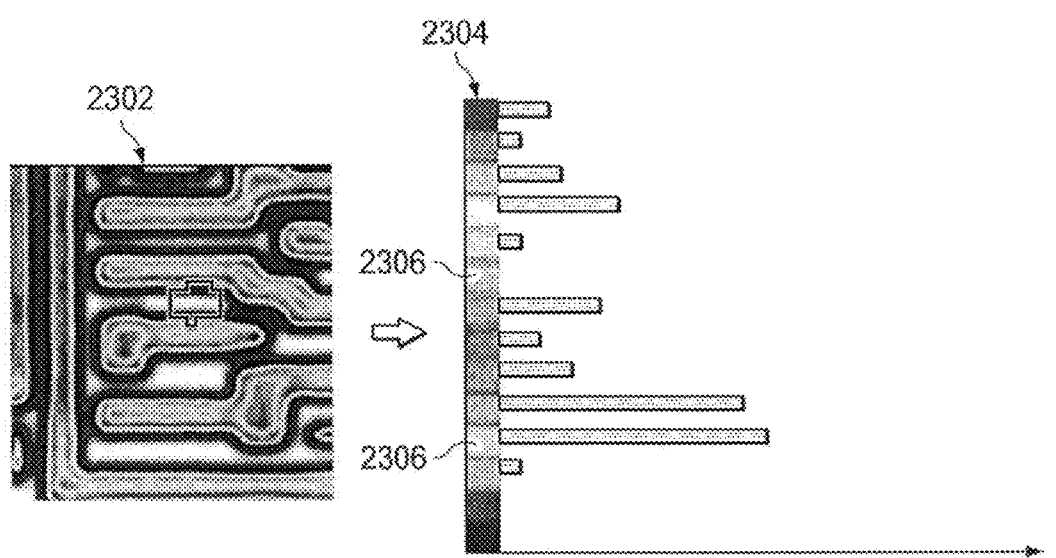

FIG. 23 is also illustrative of binning and includes a gray scale image 2302 and an associated binning result 2304 indicating the occurrence of various values (e.g., levels of gray) 2306 within the image (or designated portion thereof). The occurrence of the gray-level may be quantified by a single pixel, a plurality of pixels (e.g., a 3×3 grouping of pixels), and/or other selected sized area of the image. For example, in an embodiment, a single pixel gray level is determined and added as one count for the gray level 2206. In another embodiment, a gray level of a group of pixels (e.g., an average gray level of the group of pixels) is determined and one count for the associated gray level 2206 provided.

As indicated above, the binning of the image may be performed on the image of the substrate in its entirety or a portion thereof. In an embodiment, the image may be divided into grid regions as described above with reference to block 1908 and the binning performed on one or more grid regions.

Figure 24:
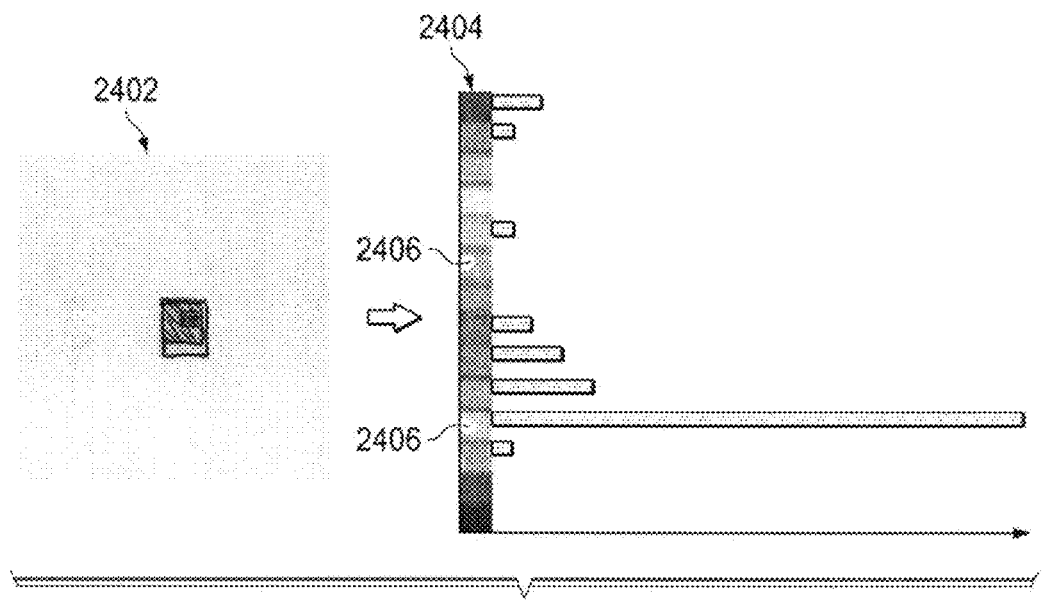

In another embodiment, the binning performed may be based on the result of a comparison of the image provided in block 1906 and a baseline image. In an embodiment, the images are converted to a gray level image and the baseline gray level subtracted from the gray level of the image of block 1906 to determine a "difference" in gray level. Referring to the example of FIG. 24, a gray-level difference image 2402 is provided. The gray-level difference image may be the result of subtracting a gray-level image of a scan of a baseline substrate from a gray-level image of the substrate provided in block 1902. The binning result 2404 illustrates the count of various levels of gray provided by the gray-level difference image 2402. For example, in an embodiment, a single pixel level is determined and added as one count for the gray level 2406. In another embodiment, a gray level of a group of pixels (or average gray level of the group of pixels) is determined and one count for the associated gray level 2406 provided.

Figure 25:
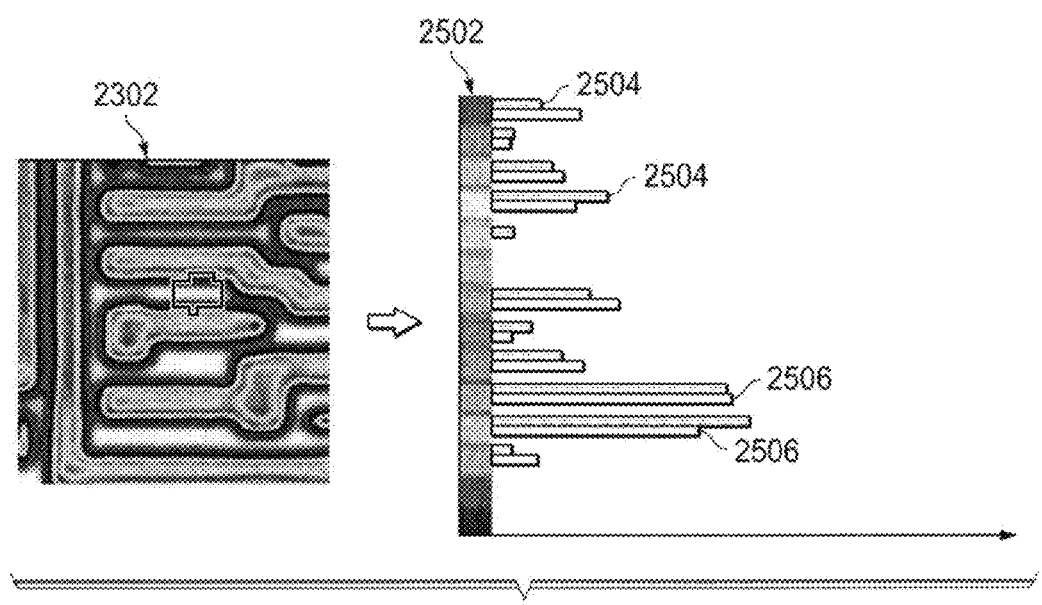

The method 1900 then proceeds to block 1918 where the binning result provided by the analysis for the image provided by the scan report of block 1906 is compared with a baseline image (e.g., a binning result of a baseline image). In embodiments of the method 1900, block 1918 is omitted (e.g., including in the embodiment discussed above with reference to FIG. 24). The comparison of block 1918 may include determining a difference in counts or occurrences of one or more groupings in the binning results. FIG. 25 is exemplary and includes a binning result 2502 in gray-level. The binning result includes the binning count of the given gray-level occurrences of the image 2502 denoted as 2504 and the binning count of the given gray-level occurrences of a baseline image denoted as 2506. Referring to the example of FIG. 18, blocks 1916 and/or 1918 may be performed by the image analysis system 1806. One example of the image analysis system 1806 is the information handling system 2700, discussed below with reference to FIG. 27.

The method 1900 then proceeds to block 1914 where binning result discussed above with reference to block 1916 and/or block 1918 may be tracked by a statistical process control (SPC) chart. FIG. 26 is illustrative of an exemplary SPC chart 2600. In an embodiment, the SPC chart may track the binning count of one or more of the groupings in the binning result (e.g., a specific gray-level or pseudo color). In an embodiment, the SPC chart may track a difference in binning counts between one or more groupings of the binning result of the analysis of the image described in block 1916 and a binning result associated with a baseline image.

Figure 27:
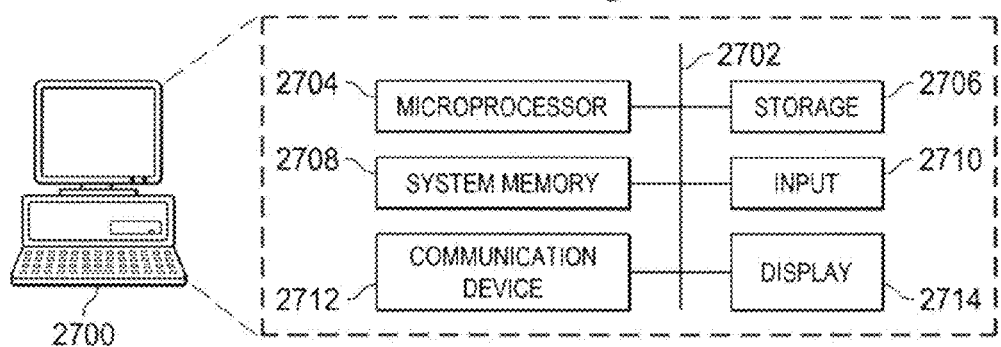
FIG. 27 illustrates a block diagram of an embodiment of an information handling system operable to implement one or more aspects of the present disclosure.

Referring now to FIG. 27, an information handling system 2700 is illustrated. In an embodiment, the information handling system 2700 includes functionality providing for one or more steps of the methods of scanning substrates, providing images, storing images, analyzing images, calculating values, comparing values, comparing images, storing simulation programs, performing simulations, performing SPC, and the like described above with reference to FIGS. 1-26. The methods may be performed by any number of information handling systems 2700 in communication, or by a single system.

The information handling system 2700 includes a microprocessor 2704, an input device 2710, a storage device 2706, a system memory 2708, a display 2714, and a communication device 2712 all interconnected by one or more buses 1902. The storage device 2706 may be a floppy drive, hard drive, CD-ROM, optical device or any other storage device. In addition, the storage device 2706 may be capable of receiving a floppy disk, CD-ROM, DVD-ROM, or any other form of computer-readable medium that may contain computer-executable instructions. The communications device 2712 may be a modem, a network card, or any other device to enable the computer system to communicate with other nodes. It is understood that any computer system 2700 could represent a plurality of interconnected computer systems such as, personal computers, mainframes, smartphones, and/or other telephonic devices.

The information handling system 2700 includes hardware capable of executing machine-readable instructions as well as the software for executing acts (typically machine-readable instructions) that produce a desired result. Software includes any machine code stored in any memory medium, such as RAM or ROM, and machine code stored on other storage devices (such as floppy disks, flash memory, or a CD ROM, for example). Software may include source or object code, for example. In additional software encompasses any set of instructions capable of being executed in a client machine or server. Any combination of hardware and software may comprise an information handling system. The system memory 2708 may be configured to store a design database, algorithms, images, graphs, simulations, and/or other information.

Computer readable medium includes non-transitory medium. Computer readable mediums include passive data storage, such as RAM as well as semi-permanent data storage such as a compact disk read only memory (CD-ROM). In an embodiment of the present disclosure may be embodied in the RAM of a computer to transform a standard computer into a new specific computing machine. Data structures are defined organizations of data that may enable an embodiment of the present disclosure. For example, a data structure may provide an organization of data, or an organization of executable code. Data signals could be carried across transmission mediums and store and transport various data structures, and thus, may be used to transport an embodiment of the present disclosure.

The information handling system 2700 may be used to implement one or more of the methods and/or systems described herein. In particular, the information handling system 2700 may be operable to receive, store, manipulate, analyze, and/or perform other actions on an image provided by an image acquiring system.

In summary, the methods and systems disclosed herein provide for the characterization of a defect based on an image of a substrate. In doing so, some embodiments of the present disclosure offer several advantages over prior art devices. Advantages of the present disclosure include the automatic characterization of a defect. For example, when a defect is illustrated in an image as similar to a pattern on the substrate, it may be difficult for a user to identify the defect. However, the analysis which may be performed by information handling systems of the present disclosure allows for quick identification and characterization of the defect. For example, the defect may be characterized as one that will image onto a photosensitive layer, a killer defect, and/or other characterizations. Further, embodiments of the present disclosure offer advantages of the comparison of initial and subsequent images of a substrate during its use and/or fabrication. This allows for a quick understanding of when and how a substrate must be reworked, cleaned, etc. Finally, embodiments of the present disclosure offer advantages of providing a monitor function to identify defects of a substrate.

Thus, one will recognize that the present disclosure provides in a broader embodiment, a method including providing a first image and a second image. The first image is of a substrate having a defect and the second image is of a reference substrate. A difference is determined between the first image and the second image. A simulation model is then used to generate a simulation curve corresponding to the difference. The substrate may be dispositioned (e.g., determined what action or corrective action to take) based on the simulation curve.

In a further embodiment, the simulation model is based on a pattern-type formed on the substrate. The simulation curve may be used to determine a type of defect. The method may be applied to embodiments where the substrate is a photomask substrate or a semiconductor device substrate.

In an embodiment, providing the first and the second images further includes providing a first pseudo-color image and a second pseudo-color image and converting the first and second pseudo-color images to first and second gray-scale images respectively. In doing so, determining the difference between the first image and the second image may include subtracting a gray-level provided by the second gray-scale image from a gray-level provided by the first gray-scale image. In an embodiment, the simulation curve includes a plot of intensity for a region corresponding to the difference between the first and second images.

In a further embodiment, the method includes generating the simulation model which may include storing a third image of a third substrate having a first pattern and a first set of intensity data provided by a scan of the third substrate and a fourth image of a fourth substrate having the first pattern and a second set of intensity data provided by a scan of the fourth substrate.

In another of the broader embodiments described herein, a method includes providing a first pseudo-color image and a second pseudo-color image. The first pseudo-color image is of a substrate scanned at a first point in time and the second pseudo-color image is of the substrate scanned at a second point in time—at least one day later than the first point of time. A difference between the first pseudo-color image and the pseudo-color second image is then determined. The difference can be provided as a gray-level value that represents a defect of the substrate at the second point in time. The gray-level value may be provided to a simulation model to generate a simulation output curve or intensity profile associated with the gray-level value. The intensity profile may provide for a determination as to whether the defect will image onto a photosensitive material in a photolithography process.

In a further embodiment, the method includes generating the simulation model by storing a second image of a second substrate and a first set of intensity data provided by a scan of the second substrate and a third image of a third substrate and a second set of intensity data provided by a scan of the third substrate. In one embodiment, the first and second sets of intensity data include data from an Aerial Image Measurement System (AIMS). In another embodiment, the first and second sets of intensity data include finite element model (FEM) data associated with a semiconductor wafer. In an embodiment, the substrate is a transparent substrate with a pattern of attenuating material disposed on the transparent substrate (e.g., a photomask).

In yet another embodiment described herein, a method includes providing a substrate and performing an inspection scan of the substrate. The inspection scan provides an image of the substrate. A statistical process control (SPC) chart is then generated using the image. The SPC chart may be based on a comparison of the baseline image and the formed image of the semiconductor substrate.

In a further embodiment, the method includes determining a difference between the image and a baseline image by separating the image into a plurality of grid regions, selecting one of the plurality of grid regions, and comparing the selected grid region with a corresponding coordinate of the baseline image. In another further embodiment, the method includes determining a difference with respect to the baseline image by defining a plurality of categories, determining a first count of each of the plurality of categories (the first count is associated with the image) and receiving a second count of each of the plurality of categories (the second count is associated with a baseline image). The first count and the second count are compared for at least one of the plurality of categories. The plurality of categories may include colors associated with a pseudo color image or gray-levels associated with a grayscale image. In a further embodiment, the generating the SPC chart includes plotting the difference between the first count and the second count. Any one of these comparisons and/or analysis of the generated image may be performed simultaneously to generated one or more SPC charts.

In a further embodiment, the method also includes defining a plurality of categories associated with the image; determining a count of at least one of the categories (the count provides an indication of a number of occurrences of the category in the image); and generating the SPC chart by plotting the count.

These embodiments are exemplary only and merely discussed to illustrate some embodiments of the disclosure discussed in detail above.

What is claimed is:

1. A method, comprising:
providing a first pseudo-color image and a second pseudo-color image, wherein the first pseudo-color image is of a substrate scanned at a first point in time and the second pseudo-color image is of the substrate scanned at a second point in time, wherein the second point in time is at least one day later than the first point of time;
determining, using an image analysis computing system, a difference between the first pseudo-color image and the pseudo-color second image, wherein the difference is provided as a gray-level value and wherein the difference represents a defect of the substrate at the second point in time;
providing the gray-level value to a simulation model to generate an intensity profile associated with the gray-level value; and
using the intensity profile to determine if the defect will image onto a photosensitive material in a photolithography process.

2. The method of claim 1, further comprising:
generating the simulation model, wherein the generating the simulation model includes storing:
a second image of a second substrate and a first set of intensity data provided by a scan of the second substrate;
a third image of a third substrate and a second set of intensity data provided by a scan of the third substrate.

3. The method of claim 2, wherein the first and second sets of intensity data include data from an Aerial Image Measurement System (AIMS).

4. The method of claim 2, wherein the first and second sets of intensity data include finite element model (FEM) data associated with a semiconductor wafer.

5. The method of claim 2, wherein the substrate is a transparent substrate with a pattern of attenuating material disposed on the transparent substrate.

6. A method, comprising:
receiving a baseline image obtained from a reference substrate;
performing an inspection scan of a semiconductor substrate, wherein the inspection scan includes using an imaging device to form an image of the semiconductor substrate;
comparing the baseline image and the formed image of the semiconductor substrate, wherein the comparing the baseline image and the formed image includes finding a difference between the formed image and the baseline image, wherein determining the difference includes:
separating the formed image into a plurality of grid regions;
selecting one of the plurality of grid regions; and
comparing the selected grid region with a corresponding coordinate of the baseline image; and generating a statistical process control (SPC) chart based on the comparison.

7. The method of claim 6, wherein the determining of the difference further includes:
defining a plurality of categories;
determining a first count of each of the plurality of categories, wherein the first count is associated with the formed image;
receiving a second count of each of the plurality of categories, wherein the second count is associated with the baseline image; and
comparing the first count and the second count for at least one of the plurality of categories.

8. The method of claim 7, wherein the plurality of categories include at least one of colors associated with a pseudo color image and gray-levels associated with a grayscale image.

9. The method of claim 7, wherein the generating the SPC chart includes plotting the difference between the first count and the second count.

10. The method of claim 6, further comprising:
defining a plurality of categories associated with the formed image;
determining a count of at least one of the categories, wherein the count provides an indication of a number of occurrences of the category in the image; and generating a second SPC chart by plotting the count.

* * * * *